United States Patent
Aquino Olivos et al.

(10) Patent No.: US 9,772,269 B2
(45) Date of Patent: Sep. 26, 2017

(54) PROCESS FOR DETERMINING THE INCOMPATIBILITY OF CRUDES MIXTURES CONTAINING ASPHALTENE

(71) Applicant: INSTITUTO MEXICANO DEL PETROLEO, Mexico City (MX)

(72) Inventors: Marco Antonio Aquino Olivos, Mexico City (MX); Adriana de Jesus Aguirre Gutierrez, Mexico City (MX); Jose Luis Mendoza De La Cruz, Mexico City (MX); Blanca Estela Garcia Flores, Mexico City (MX); Jacinto Aguila Hernandez, Mexico City (MX); Veronica Ramos Corzo, Mexico City (MX); Juan Carlos Cedillo Ramirez, Mexico City (MX)

(73) Assignee: INSTITUTO MEXICANO DEL PETROLEO, Mexico City (MX)

( * ) Notice: Subject to any disclaimer, the term of this patent is extended or adjusted under 35 U.S.C. 154(b) by 278 days.

(21) Appl. No.: 14/560,483

(22) Filed: Dec. 4, 2014

(65) Prior Publication Data
US 2015/0160109 A1    Jun. 11, 2015

(30) Foreign Application Priority Data

Dec. 6, 2013 (MX) .................... MX/a/2013/014349
Dec. 6, 2013 (MX) .................... MX/a/2013/014351

(51) Int. Cl.
*G01N 9/36*    (2006.01)
*G01N 11/14*   (2006.01)
*G01N 33/28*   (2006.01)
*G01N 9/00*    (2006.01)

(52) U.S. Cl.
CPC ............... *G01N 9/36* (2013.01); *G01N 9/002* (2013.01); *G01N 11/14* (2013.01); *G01N 33/2823* (2013.01); *G01N 33/2835* (2013.01)

(58) Field of Classification Search
CPC ...................................................... G01N 9/36
See application file for complete search history.

(56) References Cited

U.S. PATENT DOCUMENTS

| | | | |
|---|---|---|---|
| 4,627,272 A | 12/1986 | Wright | |
| 4,853,337 A | 8/1989 | Dickakian | |
| 4,864,849 A | 9/1989 | Wright | |
| 5,025,656 A | 6/1991 | Wright | |
| 5,871,634 A | 2/1999 | Wiehe et al. | |
| 5,997,723 A | 12/1999 | Wiehe et al. | |
| 6,584,831 B1 | 7/2003 | Kasameyer et al. | |
| 7,029,570 B2 | 4/2006 | Mason et al. | |
| 7,618,822 B2 | 11/2009 | Nemana et al. | |
| 2016/0097757 A1* | 4/2016 | Sieben | G01N 1/28 436/60 |

* cited by examiner

*Primary Examiner* — Clayton E Laballe
*Assistant Examiner* — Dennis Hancock
(74) *Attorney, Agent, or Firm* — Dickinson Wright PLLC

(57) ABSTRACT

Density measurement of mixtures of heavy and light crudes using the vibrating tube densitometer technique determine incompatibility in the crudes mixture containing asphaltenes by determining the incipient point of asphaltenes incompatibility threshold in the mixtures of crudes.

11 Claims, 2 Drawing Sheets

PROCESS FOR DETERMINING THE INCOMPATIBILITY OF CRUDES MIXTURES CONTAINING ASPHALTENE

CROSS-REFERENCE TO RELATED APPLICATIONS

This application claims the benefit and priority under 35 U.S.C. §119 to Mexican Patent Application No. MX/a/2013/014351 with a filing date of Dec. 6, 2013, and Mexican Patent Application No. MX/a/2013/014349 with a filing date of Dec. 6, 2013, the disclosures of which are incorporated herein by reference in their entirety.

Reference is hereby made to copending U.S. application Ser. No. 14/560,520 to Marco Antonio AQUINO OLIVOS et al., filed Dec. 4, 2014, the disclosure of which is hereby incorporated by reference in its entirety.

FIELD OF THE INVENTION

This invention relates to a process for determining the incompatibility of asphaltene-containing crude mixtures. More particularly, the invention relates to a process for determining the incompatibility of mixtures of an asphaltene-containing mixture of heavy and light crudes at a constant temperature and pressure using the vibrating tube densitometer technique.

The mixing process of crudes includes the procedure to determine the incipient point of asphaltenes incompatibility in crudes mixture.

BACKGROUND OF THE INVENTION

The study of petroleum analysis and its products would be incomplete without considering the incompatibility phenomenon in the crudes mixtures that causes changes in the original properties therein; i.e. during and after the crudes mixing, secondary products such as sludge, semisolids or solid particles increasing its viscosity and density, can be formed.

In short, the term incompatibility refers to the formation of a precipitate or sediment, or the separation of phases when the liquids are mixed.

Normally, the incompatibility processes in the crudes mixing increase petroleum or petroleum products viscosity, and it causes changes of viscosity in certain fuels even at low temperatures.

Some studies prove that the mixing of different crudes can lead to a flocculation/precipitation of asphaltenes. This phenomenon, known as crudes incompatibility causes more problems in the transportation and refinement, especially when the economical situation is forcing the refineries to carry out low cost crudes mixing to increase refining margins.

In spite of various studies carried out in the last decades, there are still important questions for chemical and physical knowledge of the incompatibility phenomenon. It is well known that this problem has not yet resulted into a standard method intended for the determination and quantification of incompatibility of crudes mixtures. Hence, several criteria for determining the crudes incompatibility are described in the literature.

On the other hand, the measurement of excess volumes started in 1983 by Dr. J. C. Cobos, ex-Laboratoire de Thermodynamique et Cinétique Chimique, now Laboratoire de Thermodynamique et Genie Chimique de L'Université Blaise Pascal (Clemront-Ferrant, France), using mechanical oscillation densitometer developed by Picker, Tremblay and Jolicoeur. At the beginning, there were two Picker models; in the first model the mechanical part was separated from the electronic part, presenting two modules, whereas in the second model both parts were included in only one module.

In 1986, the Thermodynamics group then called Thermology Department, now Thermodynamics Department and Applied Physics, acquired a densitometer based on the model of Stabinger, Leopold and Kraky. The vibrating element in this densitometer is a U shaped borosilicate tube that had a coil with heat exchanger function and that allow to work dynamically. Furthermore, a unit receiving oscillating signal was added to the densitometer, signal emitted by the densitometer output; afterwards, this second unit was substituted by a frequency meter.

J. F. Rodriguez made the data acquisition software and subsequently those of A. Cerna. F. J. Carmona and F. J. Arroyo followed. These last two added a temperature sensor to record temperature at which the liquid contained in the U shaped tube is contained, but as it was constantly breaking, it was necessary to substitute the cell containing it by the another one without coil and that allowed to carry out measurements at pressures up to 5 MPa.

The density of a homogenous substance is a physical property that characterizes it and is defined as the ratio between the substance mass and volume concerned. This property depends of the temperature that is why by measuring the density of a substance, the temperature at which measuring is carried out, must be considered.

In the case of non-homogenous substances, what is obtained is the mean density of the division of the mass and volume.

The incompatibility phenomenon of the petroleum-derived products is invariably associated with the chemical composition and physical relation of the components. In most cases, a certain component added to one of the fuels reacts with another component in the fuel with the one that is mixed. This chemical reaction results in the formation of a new product that, when is soluble, affects the mixing properties and when it is insoluble, is deposited as a semisolid or solid matter. Based on the above, different studies were carried out to determine, qualify, inhibit or prevent the formation of asphaltenes during manufacture, transportation and petroleum refining.

U.S. Pat. No. 7,029,570, dated Apr. 18, 2006, refers to a process for determining the incompatibility in crudes mixtures through the change in the dispersion length density of neutrons in the surface of asphaltene aggregates.

Carrier et al. in "*Acoustic method for measuring asphaltene flocculation in crude oils*", Journal of Petroleum Science and Engineering 27 (2000), pp. 111-117, evaluated the presence of asphaltenes in crudes and developed an experimental device, based on an acoustic technique, for testing. In opaque systems, as the oil, the optical methods cannot be used to carry out its characterization that is why the transition of phases can be directly carried out, identifying breaking, discontinuity or the change of slopes of certain physical characteristics that accompany the change of phases, when temperature, pressure or composition of the system are altered.

Ekulu et al. in "*Scanning Aggregation Phenomena in Crude Oils with Density Measurements*", Journal of Dispersion Science and Technology Vol. 25, No. 3, pp. 321-331, 2004, demonstrated that the density measurements can be used to evaluate changes of aggregation that are produced in a crude under the influence of chemical and physical factors. Apparent volumes and reduced densities are used to obtain graphs that clearly indicate the different steps of the aggregation phenomenon; the characteristic points of the graphs correspond to the well known phenomena that are produced in the crude, such as the flocculation incipient point of asphaltenes is called Critical Micellar Concentration (CMC). Also system density measurements were used (crude–toluene–n-heptane) for the determination of the flocculation incipient point of various crudes. This method was verified with flocculation data obtained with already established methods.

Tharanivasan et al. in "*Measurement and Modeling of Asphaltene Precipitation from Crude Oil Blends*", Energy & Fuels 2009, 23, 3971-3980, developed a model using the regular solution theory to predict the appearance and quantity of precipitated asphaltenes of crude mixtures with pure n-alkanes or a toluene and n-heptane mixture. The tests were carried out with nine different crudes, a gasoil and its mixtures. The crudes and the mixtures were characterized in terms of SARA (saturated, aromatic, resins and asphaltenes) analysis fractions.

The references described in the state of the art, known by the applicant, were overcome through the present invention, since up to now there is not any reliable technique agreed to determine the incompatibility of heavy metals with light crudes.

An object of the present invention is to provide a reliable technique to determine incompatibility of heavy crudes with light crudes so as to be able to determine the proportions of light and heavy crudes suitable for mixing. Another object of the invention is to measure mixture densities of heavy crudes with light crudes at different temperature and pressure conditions.

Another object of the present invention is to measure the density of crudes mixtures with light crudes through a system or vibrating tube densitometry that provides quick and reliable results with uncertainty in the density measurement of 1 kg/m$^3$, using 25 mL of sample.

The above and other objects of the present invention are provided as follows:

SUMMARY OF THE INVENTION

The present invention comprises a process for determining the incompatibility of an asphaltene-containing crude oil mixture comprising heavy crude and light crude, which process comprises forming mixtures of heavy crude and light crude, the mixtures containing asphaltenes, and determining the incipient point of asphaltene incompatibility by density measurement of varying concentrations of light crude in the heavy crude.

According to a preferred embodiment of the invention, the crude mixture is made of heavy crude of 10 to 22.3° API and light crude of °API>31.1, at a temperature of 293 to 423 K and pressure of 0.1 to 68.9 MPa.

According to a further embodiment of the invention the process for determining the incompatibility of asphaltene-containing heavy crudes in admixture with light crude, which comprises:

a) formation of mixtures of asphaltene-containing heavy crude and light crude;

b) loading the mixtures of crudes into a high pressure stainless steel container of a measuring system;

c) transfer of the crude mixture contained in the high pressure stainless steel container to a measuring circuit;

d) determination of density ($\rho$) of the crude mixtures;

e) monitoring of density of the crude mixtures; and f) determination of the incipient point of asphaltenes incompatibility threshold in the crude mixtures, based on the behavior of the mixture density ($\rho$) based on the amount of added light crude.

According to another embodiment of the invention, the present process uses a sample volume of 25 mL to measure the crudes mixture density and provides quick and reliable results with an uncertainty or margin of error in the density measurement of 1 kg/m$^3$.

DETAILED DESCRIPTION OF THE INVENTION

Figure 1:
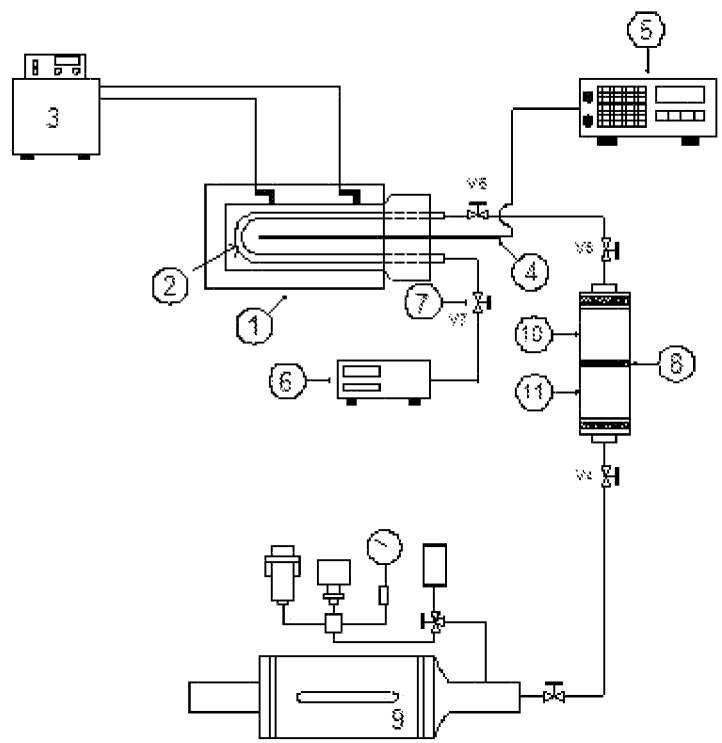
FIG. 1 shows the flow diagram of the density measuring system of the vibrating tube densitometer of the present invention.

The present invention comprises a process employing measurements of densities of heavy and light crudes mixtures at constant temperature and pressure, using the vibrating tube densitometer technique in order to determine the incompatibility in crudes mixtures containing asphaltenes; wherein the crudes mixtures are preferably carried out with heavy crude of 10 to 22.3° API and light crudes of °API>31.1, at a temperature of 293 to 423 K and pressure of 0.1 to 68.9 MPa.

The crudes mixing process includes the procedure for determining the incipient point of asphaltene incompatibility threshold in crudes mixtures. The present process can be used to determine the incipient point of an asphaltene-containing hydrocarbon mixture or blend, preferably involving heavy crude and a lighter hydrocarbon. Preferably, the present process is applicable to an asphaltene-containing mixture or blend of a heavy crude with a lighter hydrocarbon, and more preferably a light crude oil that when mixed or blended with a heavy crude can result in the precipitation of asphaltenes from the mixture or blend. Thus, the term light crude as used can be any hydrocarbon fraction having an API gravity greater than 20 or greater than 30, preferably between 31 and 42, or more preferably between 31.2 and 38.9. The process of the present invention for determining the incompatibility in heavy crudes of light crude mixtures containing asphaltenes, is preferably characterized by:

The heavy crudes tested have an API gravity from 10 to 22.3 units;

The light crudes have an API gravity greater than 31.1 units (>31.1);

The density measurement of crudes mixture is carried out at constant temperature and pressure:

The range of conditions at which preferably the crudes mixture density measurement is carried out is: temperature of 293 to 423 K and pressure of 0.1 to 68.9 MPa;

Uses the vibrating tube densitometer technique to measure the density of the crudes mixtures;

Uses a sample volume of 25 mL to measure the density of the crude mixtures;

Provides quick and reliable results with an uncertainty in the density measurement of 1 kg/m$^3$; and The determination of the incipient point of asphaltene incompatibility threshold in the crude mixtures is carried out through graphic observation of the slope change of the density behavior ($\rho$) of the sample vs. the added light crude volume (%).

The process of the invention for determining incompatibility in crudes mixtures containing asphaltenes, comprises the following steps:

A. Preparation of homogenous mixtures of heavy and light crudes;

B. Loading 25 mL of crudes mixture to the high-pressure stainless steel container of the measuring system and its connection to the measuring circuit;

C. Isothermal and isobaric transfer of crude mixture contained in the high pressure stainless steel container to the measuring circuit;

D. Determination of the density of crudes mixture ($\rho$) at a constant temperature and pressure, temperature from 293 to 423 K and pressure of 0.1 to 68.9 MPa;

E. Monitoring of crudes mixture density, based on the percentage of added light crude volume; and F. Determination of the incipient point of the asphaltene incompatibility threshold in the crude blend, based on the blend density behavior ($\rho$), based on the added light crude; more specifically, through the graphic behavior of the slope change of the blend density slope vs. added light crude volume (%). By determining the incipient point of asphaltene incompatibility, one can add a predetermined volume of light crude below such incipient point to include in the heavy crude/light crude mixture to provide desired pumpability and/or storability of the heavy crude/light crude mixture without encountering aggregation and precipitation of the asphaltenes that cause pipe blockage and related problems.

The measuring system of vibrating tube densitometer of the present invention, FIG. 1, is particularly easy from the mechanical point of view and the basic principle for determination of density is effective.

According to FIG. 1, the density measurement system or the vibrating tube densitometer of the invention comprises:

1) A measuring cell, for example: Anton Paar DMA 512 P cell, to measure temperatures up to 423 K and pressures of up to 68.9 MPa, connected to an evaluation unit, for example: DMA 60 unit;
2) A U shaped high pressure stainless steel tube;
3) A liquid recirculating bath to thermo-regulate the measuring cell (1);
4) A platinum probe connected to a temperature gauge (5);
5) A temperature indicator;
6) A digital pressure transducer;
7) A vacuum pump that allows to remove any air trace in the experimental system;
8) A high pressure stainless steel container with a floating piston for sample feed;
9) A positive displacement pump that allows to transfer the sample to the system and generate the desired pressure;
10) Crudes blend contained in the high pressure stainless steel (8); and
11) Pressurization fluid.

The density measuring system by the vibrating tube method is reliable by being stable, quick and very easy to configure and use. This technique is an indirect method and was satisfactorily used for more than 20 years in the determination of pure compounds liquids and mixtures. The basic theory and operation principle to determine the density of liquid using the vibrating tube densitometer have been widely described in the literature. A similar system is described in the doctoral thesis entitled "DETERMINACIÓN EXPERIMENTAL DE LA INCOMPATIBILIDAD/COMPATIBILIDAD DE MEZCLAS DE HIDROCARBUROS MEDIANTES LAS TÉCNICAS DE VISCOMETRÍA Y DENSIMETRÍA", 77 pages, Escuela Superior de Ingeniería Química e Industrias Extractivas, Instituto Politécnico Nacional by Juan Carlos CEDILLO RAMÍREZ, Published on Jan. 28, 2013, the disclosure of which is hereby incorporated by reference in its entirety.

The present invention is based on system density measurements {crude+toluene+n-heptane} to evaluate the aggregation changes that occur in a crude under the influence of chemical and physical factors.

Ekulu et al. in "*Scanning Aggregation Phenomena in Crude Oils with Density Measurements*", Journal of Dispersion Science and Technology Vol. 25, No. 3, pp. 321-331, 2004, researched the effect of compositional changes in the aggregation and in the asphaltene flocculation incipient point; the obtained results made possible to determine the start of asphaltenes flocculation for various crudes, based on mixtures density changes, quantifying the changes in the molecular packing of crude components. Also, they found that n-heptane increased the molecular packing of the crudes, but also increased the packing of asphaltene-free crudes. Toluene also increases the molecular packing. Therefore, the aggregation phenomenon that occurs in crudes not only concerns the asphaltenes but also other crude components.

The incipient point of asphaltenes incompatibility threshold, which is an object of the present invention, is detected by an increase of crudes mixture density, wherein the aggregation of asphaltenes particles occurs.

The following describes a practical example to achieve a better understanding of the present invention, without limiting its scope.

Before including an example, it is important to mention that with the purpose to guarantee that the density measurements are reliable, the transducer of digital pressure and the temperature gauge were individually calibrated, as the density measurement system or vibrating tube densitometer of the present invention, integrally. Nitrogen (purity of 99.99%) and water (bio-distilled analysis grade) were used as calibration fluids. The maximum uncertainty in the density in temperature ranges from 313.6 to 413 K was of ±0.4 kg/m$^3$ at 65 MPa. In order to validate the calibration method, the toluene densities and benzene (GC analysis) were measured (HPLC grade) in the same temperature and pressure range. At 373.2 K, the maximum deviation in the density (0.42%) was found at 50 MPa of the value obtained by Franck et al. in "*The density of Toluene at High Pressure to 673 K and 300 Mpa*", Ber. Bunsenges, Phys. Chem. 102, 1794-1797 (1998) No. 12, in the range of 5 MPa to 50 MPa. The densities of benzene, at 313.2 K, have a good concordance with a maximum deviation of 0.17% compared with measurements of Lagourette et al. in "Densitometer calibration method versus temperature and pressure", Meas. Sci, Technol. 3 (1992) 699-703 and Sun et al. (1987) in the pressure range of 0.1 to 40 MPa. The experimental data of toluene and benzene are not included herein.

The following examples show the operation of the process and system described to determine the asphaltene incompatibility in the heavy and light crude mixture, in the range of a temperature of 293 to 423 K and pressure of 0.1 to 68.9 MPa (see FIG. 1).

Step A. Mixtures of heavy crudes (asphaltene contents of 14.9% mass with n-heptane) were prepared with light crude (asphaltene contents of 4.5 of mass with n-heptane) of 0%, 25-35%, 40-50%, 60-75% and 100% volume of light crude.

Table 1 shows the SARA (saturated, aromatic, resins, asphaltenes) analysis and API Gravity of the heavy and light crudes used in the preparation of mixtures. The asphaltene content of the crudes was obtained with n-heptane.

TABLE 1

Characterization of heavy and light crudes, used in the current invention

| Group, % mass | Heavy crude | Light crude |
|---|---|---|
| Saturated | 18.7 | 29.3 |
| Aromatic | 31.7 | 40.7 |
| Resins | 34.7 | 25.6 |
| Asphaltenes | 14.9 | 4.5 |
| ° API | 20.95 | 33.23 |

Step B. 25 mL of the heavy crude-light crude blend (10) is loaded to a high pressure stainless steel container (8) and connected to a measuring circuit through valves V4 and V5. The high pressure stainless steel container (8) contains in its interior a high pressure stainless steel piston that freely floats through the stainless steel container (8) separating the blend (10) of the pressurization fluid (11). In order to maintain a homogenous temperature in the measuring system, the high pressure stainless steel (8) is warmed with a heating resistance. The stainless steel pipelines that integrate the measuring circuit are also heated with heating tapes.

Step C. Temperature is adjusted in the system through a circulating bath (3). The temperature in the apparatus is measured by a temperature sensor (4) connected to a digital indicator (5). The pressure in the system is generated and controlled by a positive displacement pump (9) that uses a mineral oil (11) as a pressurization fluid. The pressure in the system is monitored by a digital pressure transducer (6). When temperature in the apparatus (1) is close to the measuring temperature, it is connected to a vacuum pump by V7. The valves V6 and V7 must be open during the vacuum process, whereas the valve V5 must be maintained closed. The measuring circuit is evacuated until obtaining an appropriate vacuum (generally, after 20 minutes approximately); afterwards, the valves V6 and V7 are closed. The pressure in the positive displacement (9) is established and the valves V5 and V6 are slowly opening. In order to ensure that the system was filled with the mixture, a small quantity of volume is purged by V7.

Step D. When the mixture is stabilized at a desired temperature and pressure, register the values of the vibration period for this temperature and pressure. Afterwards, the temperature is increased in the system by means of a circulating bath (3); when the measuring desired temperature and pressure are newly stabilized, register the values of the vibration period for this temperature. Repeat Step D until completing the series of measurements for different desired temperatures at a constant pressure.

Step E. Monitor the behavior of the mixture density based on the added light crude volume, at constant temperature and pressure.

Step F. If the behavior of the density vs. percentage of light crude added volume does not have a typical behavior, that is, the density decreases when diluent is added, prepare mixtures of heavy crude+light crude with percentage of light crude volume less than the inflexion point found in Step E and repeat the Steps B, C, D and E. Repeat Step F until the slope change in the mixture density behavior corresponds to the minimum percentage of added light crude, as it can be observed in FIGS. Nos. 2 and 3; the immediately preceding point to the slope change or inflexion point of the density is considered as the threshold incipient point of asphaltenes incompatibility.

Table 2 shows the characterization of an optimum mixture of heavy crude and light crude before the incompatibility phenomenon of crude mixtures occurs.

TABLE 2

Characterization of heavy crude optimum mixture with light crude

| Group, % mass | Heavy crude optimum mixture with light crude |
|---|---|
| Saturated | 22.73 |
| Aromatic | 40.70 |
| Resins | 24.29 |
| Asphaltenes | 12.25 |
| ° API | 28.60 |

Figure 2:
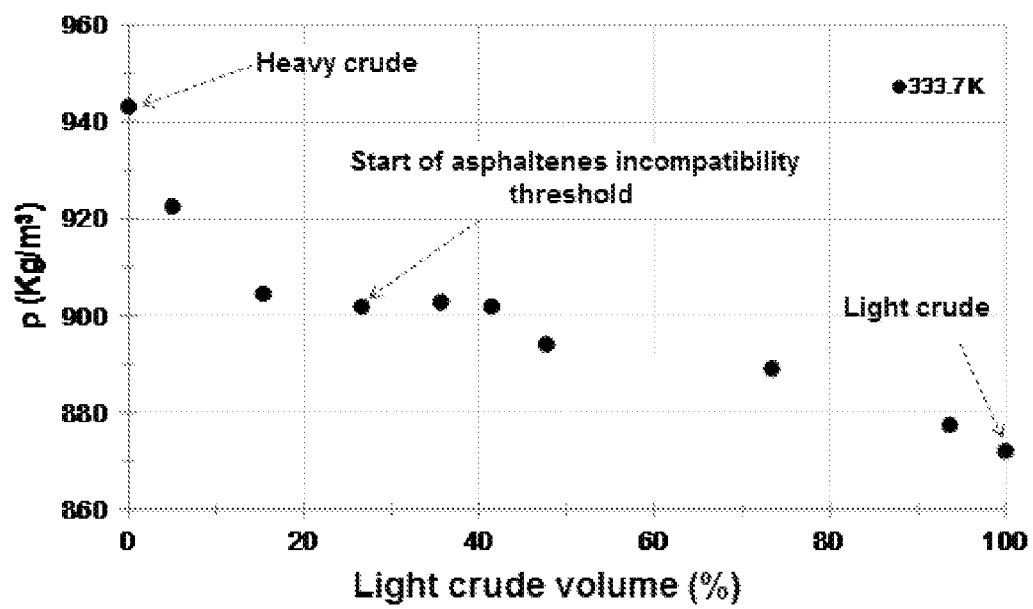
FIG. 2 shows the results of density obtained for heavy crude mixtures with light crude, from 0 to 100% volume of light crude, including the start of the asphaltene incompatibility threshold object of the present invention, as well as densities of heavy and light crude at a temperature of 333.7 K to 0.1 MPa.

FIG. 2 illustrates the densities measured in various mixtures (heavy crude light crude) from 0 to 100% volume of light crude. Under low fractions of added light crude volume (up to ~15%), the density gradually decreases and afterwards experiences an increase of density when the light crude volume fraction exceeds 26.6%; this increase of the density reaches a maximum value and subsequently the density of the mixture slowly decreases.

Based on research of Ekulu et al. in "*Scanning Aggregation Phenomena in Crude Oils with Density Measurements*", Journal of Dispersion Science and Technology Vol. 25, No. 3, pp. 321-331, 2004 and the criteria described by Escobedo and Manssori in "*Viscometric Determination on the Onset of Asphaltene Flocculation: A Novel Method*", Society of Petroleum engineers (SPE) Production & Facilities, May 1995, the incipient point of the asphaltenes incompatibility threshold was found at 26.6 volume % of light crude in the mixture. In other words and based on the previous description, it can be concluded that the start of an asphaltene incompatibility threshold corresponds to the immediately previous point when density increases.

Figure 3:
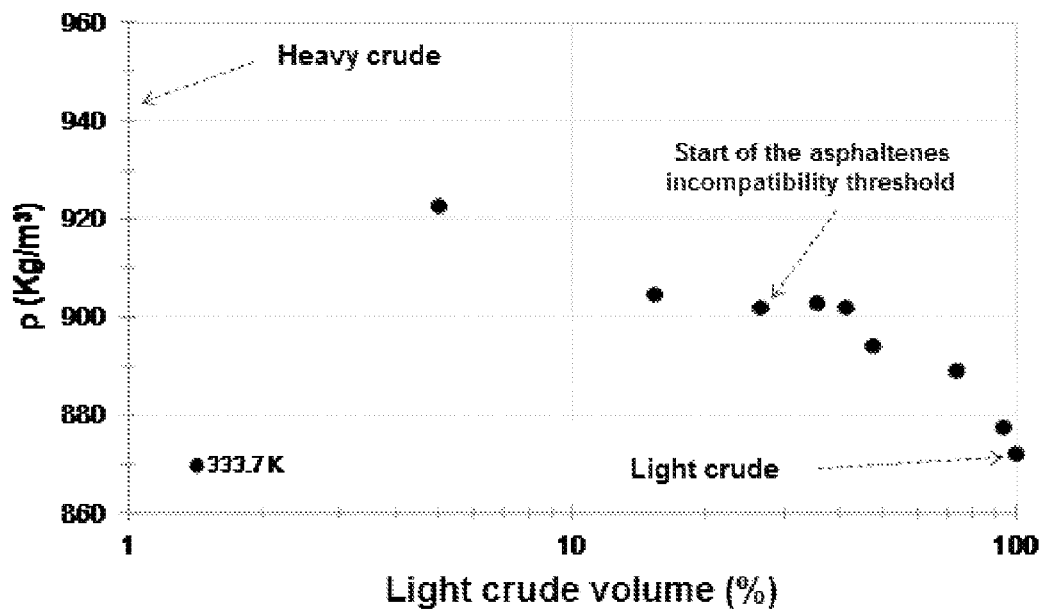
FIG. 3 shows, in logarithmic coordinates in the X-axis, the densities of heavy crude mixtures with light crude added in excess, including the start of asphaltenes incompatibility threshold, which is an object of the present invention, at a temperature of 333.7 and 0.1 MPa.

FIG. 3 shows, in logarithmic scale on the X-axis, the incipient point of asphaltene incompatibility, as well as the behavior of the density in system mixtures (heavy crude+ light crude) when it is added in excess to the light crude.

Figure 4:
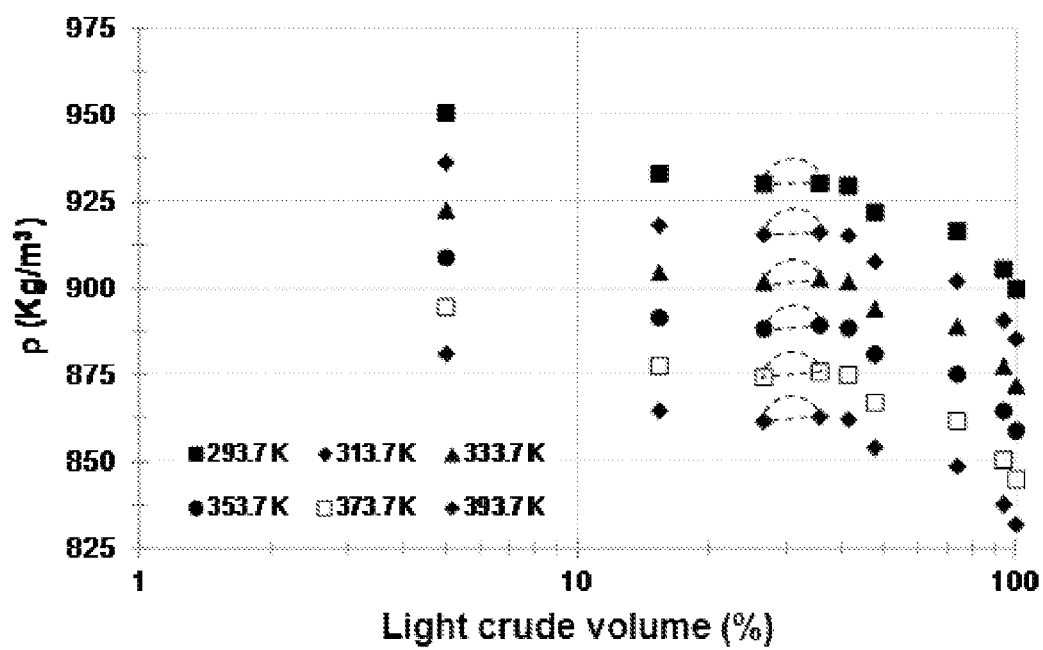
FIG. 4 shows, in logarithmic coordinates in the X-axis, six density isotherms in the temperature range of 293 to 393 K and at a constant pressure of 0.1 MPa, including the asphaltene incompatibility threshold, which is an object of the present invention, for heavy and light crudes mixtures.

FIG. 4 shows, in logarithmic scale on the X-axis, that the density isotherms vs. light crude volume fraction had the same behavior at different temperatures, i.e., firstly a decrease of mixture density until obtaining a minimum value and afterwards an increase in the asphaltenes incompatibility threshold. This figure shows the incipient point of the asphaltenes incompatibility threshold, measured for heavy crudes and light crudes blends, at six different temperatures and 0.1 MPa. In the range of temperature of 293.7 and 393.7 K, the incipient point starts when the fraction of light crude in the blend is of 26.6% volume. The dotted region in FIG.

4 delimits the asphaltenes incompatibility threshold for each temperature. It is evident that the asphaltenes are in the crude in a delicate balance and this balance can be easily disrupted by the addition of saturated crudes or by removing resins or aromatic crudes; subsequently, the crudes mixing can considerably change the global concentrations of these molecular types altering this balance and to flocculate/precipitate the asphaltenes.

Moderate quantities of asphaltenes cause pressure drops and interfere in the equipment operation, resulting in an inefficient process. Finally, large quantities of asphaltenes cause intolerable blockages or tamponades and cause the process to stop until the pipelines are cleaned. That is why it is important to find the incompatibility point (the optimum mixture) to avoid the above-mentioned problems.

What is claimed is:

1. A process for determining the incompatibility of an asphaltene-containing heavy crude in admixture with a light crude and preparing a crude oil admixture containing a heavy crude and a light crude in amounts to inhibit precipitation of asphaltenes from said admixture, said process comprising forming a plurality of mixtures of said heavy crude and said light crude at different concentrations of light crude in the respective mixture, measuring the density of said plurality of mixtures and determining the incipient point of asphaltene where asphaltene precipitate from the crude oil mixture, and adding a predetermined amount of said light crude to said admixture below the incipient point to inhibit the aggregation and precipitation of asphaltenes from said admixture.

2. A process for determining the incompatibility of asphaltene-containing heavy crudes in admixture with light crude and preparing a crude oil mixture containing a heavy crude oil and a light crude oil in amounts to inhibit precipitation of asphaltenes from said crude oil mixture, which comprises:
   a) formation of mixtures of asphaltene-containing heavy crude in admixture with different volume percentages of light crude added to the heavy crude;
   b) loading the mixtures of crudes into a high pressure stainless steel vessel;
   c) transfer of the crude mixture contained in the high pressure stainless steel vessel to a measuring circuit;
   d) determination of density ($\rho$) of the crude mixtures;
   e) monitoring of density of the crude mixtures; and
   f) determination of the incipient point of asphaltenes incompatibility threshold in the crude mixtures, based on the behavior of the mixture density ($\rho$) based on the amount of added light crude; and
      adding a predetermined amount of light crude oil to a heavy crude oil in an amount below the incipient point to inhibit the aggregation and precipitation of asphaltenes from the resulting mixture of said light crude oil and heavy crude oil.

3. The process of claim 2, wherein the crude oil mixture containing asphaltenes is carried out with heavy crude of 10 to 22.3° API and light crude >31.1° API.

4. The process of claim 2, wherein in the step a) the crude oils are mixed until homogenous mixtures are formed.

5. The process of claim 2, wherein the measuring circuit comprises:
   a) a density measuring cell for measuring temperatures and pressures and connected to an evaluation unit;
   b) a U shaped high pressure stainless steel tube within the density measuring cell;
   c) a liquid recirculating bath for regulating the temperature of the density measuring cell;
   d) a platinum cell for measuring the temperature of the recirculating bath;
   e) a temperature indicator connected to said platinum cell for displaying the temperature from the platinum cell;
   f) a digital pressure transducer for monitoring pressure in said density measuring cell;
   g) a vacuum pump for removing air from said measuring circuit;
   h) said high pressure stainless steel vessel with a floating pressure piston for receiving the crude blend and for directing the crude blend to the density measuring cell; and
   i) a positive displacement pump for maintaining a pressure in said density measuring cell.

6. The process of claim 5, wherein in the step b) the high pressure stainless steel container, is loaded with 25 mL of the crude oil mixtures.

7. The process of claim 2, wherein in the step c) the transfer of the crude oil mixture to the measuring circuit is carried out under isothermal and isobaric conditions to maintain a stable crude oil mixture.

8. The process of claim 2, wherein in the step d) the determination of the crude oil mixture density ($\rho$) is carried out at constant temperature and pressure, at a temperature from 293 to 423 K and a pressure from 0.1 to 68.9 MPa.

9. The process of claim 2, wherein in the step e) the monitoring of crude oil mixture density is carried out based on an amount by volume of light crude oil added to said heavy crude oil.

10. The process of claim 2, wherein in the step f) the determination of the incipient point of asphaltenes incompatibility in crude oil mixture is carried out through the graphical observation of the slope change of the mixture density behavior ($\rho$) vs. added light crude volume (%).

11. The process of claim 2, having a margin of error in the density measurement of 1 kg/m$^3$.

* * * * *